(12) United States Patent
Ilyin et al.

(10) Patent No.: US 10,412,957 B2
(45) Date of Patent: *Sep. 17, 2019

(54) SYSTEM, METHOD, AND DEVICE FOR PRESERVING BLOOD OR ITS COMPONENTS IN GAS MEDIUM UNDER PRESSURE

(71) Applicant: Rich Technologies Holding Company, LLC, Buffalo, NY (US)

(72) Inventors: Ilya Ilyin, Wayland, MS (US); Semyon Kogan, Newton, MA (US); William E. Grieshober, Jr., Buffalo, NY (US); Igor Kachko, Saint Petersburg (RU); Vladimir Vasiliev, Saint Petersburg (RU); Stanislav Kolchanov, Saint Petersburg (RU); Yuriy Punin, Saint Petersburg (RU); Mark Bakhrakh, Saint Petersburg (RU); Alexander N. Schumeev, Saint Petersburg (RU)

(73) Assignee: Rich Technologies Holding Company, LLC, Buffalo, NY (US)

( * ) Notice: Subject to any disclaimer, the term of this patent is extended or adjusted under 35 U.S.C. 154(b) by 87 days.

This patent is subject to a terminal disclaimer.

(21) Appl. No.: 15/413,646

(22) Filed: Jan. 24, 2017

(65) Prior Publication Data

US 2017/0127666 A1    May 11, 2017

Related U.S. Application Data

(63) Continuation of application No. 13/529,024, filed on Jun. 21, 2012, now Pat. No. 9,743,660.

(Continued)

(51) Int. Cl.
*A01N 1/02* (2006.01)
*A61J 1/10* (2006.01)
(Continued)

(52) U.S. Cl.
CPC ........... *A01N 1/021* (2013.01); *A01N 1/0242* (2013.01); *A01N 1/0263* (2013.01);
(Continued)

(58) Field of Classification Search
CPC ........................... A01N 1/0263; A01N 1/0289
See application file for complete search history.

(56) References Cited

U.S. PATENT DOCUMENTS

| | | | | |
|---|---|---|---|---|
| 3,901,083 A | * | 8/1975 | Wallace | G01L 7/02 73/715 |
| 2009/0012493 A1 | * | 1/2009 | Harig | A61M 1/0003 604/404 |

* cited by examiner

*Primary Examiner* — Ariana Zimbouski
(74) *Attorney, Agent, or Firm* — Michael Best & Friedrich LLP

(57) ABSTRACT

A system, method, and device for preserving blood and its components is described. The system and method generally include a device having a body defining a chamber, the chamber being configured to receive at least one bag containing blood or its components, the at least one bag being permeable to gas, for example, xenon. A cover is hermetically sealable to the body. An inlet is in fluid communication with the chamber. A pressure indicator is configured to indicate pressure in the chamber, the pressure indicator including a conduit containing a liquid. A portion of the conduit is transparent such that the liquid is visible. A source of pressurized gas, such as xenon, is provided to provide the pressurized gas to the chamber.

26 Claims, 4 Drawing Sheets

Related U.S. Application Data

(60) Provisional application No. 61/499,834, filed on Jun. 22, 2011.

(51) Int. Cl.
*A61J 1/16* (2006.01)
*A61M 1/02* (2006.01)

(52) U.S. Cl.
CPC .............. *A01N 1/0289* (2013.01); *A61J 1/10* (2013.01); *A61J 1/16* (2013.01); *A61M 1/0272* (2013.01); *A61M 2202/0291* (2013.01); *A61M 2202/0427* (2013.01)

SYSTEM, METHOD, AND DEVICE FOR PRESERVING BLOOD OR ITS COMPONENTS IN GAS MEDIUM UNDER PRESSURE

CROSS-REFERENCE TO RELATED APPLICATION

This application is a continuation of U.S. patent application Ser. No. 13/529,024 filed Jun. 21, 2012, which in turn claims the benefit of priority to U.S. provisional patent application Ser. No. 61/499,834, filed on Jun. 22, 2011, the disclosure of which is incorporated herein by reference.

FIELD OF THE INVENTION

The invention refers to the field of living tissue preservation and can be used for the preservation of blood or its components in a gas medium under pressure.

BACKGROUND OF THE INVENTION

It is known to preserve blood and its components using conventional gas-impermeable plastic bags for storing blood and its components. Usually such bags are produced by sealing two flat blanks by their perimeter, which permits high manufacturability of the production process and low cost. These bags are highly reliable when used in a conventional manner because only the weight of fluid inside the bag exerts pressure onto the sealed seam, which can be considered a joint. Consequently, the pressure of a gaseous medium, if any, inside the bag generally does not exceed atmospheric pressure.

However, bags for keeping and storing biological material in a gaseous medium that is under pressures that exceed atmospheric pressure are limited by the strength of the sealed joint. Taking into account the character of load exerted onto the sealed joint when the bag volume is expanded, the strength of the sealed joint must be considerable. Adequate strength could be ensured by increasing the thickness of the bag material, by selection of material that provides a monolithic sealed joint after sealing, by additional reinforcement of the bag through limiting the variation of its shape when gas is pumped into it, and by other methods. However, such methods would lead to an increase in bag cost, which is undesirable because these bags are disposable products. These methods can also lead to potential changes in bag permeability to gases (which can be important for storage of certain blood components), changes in process of its use, and the introduction of new materials (whose contact with blood could potentially have unknown consequences).

What is needed is a system, method, and/or device for using gas permeable plastic bags for storing biological fluids in a gaseous medium under pressure.

SUMMARY OF THE INVENTION

The invention may be embodied as a method of preserving blood and its components. A device may be provided, including, a body defining a chamber, a cover hermetically sealable to the body, an inlet configured to provide pressurized gas to the chamber from a gas source, and a pressure indicator configured to indicate pressure in the chamber. In one embodiment, the gas is xenon. The pressure indicator can include a conduit containing a liquid. A portion of the conduit may be transparent such that the liquid is visible. At least one bag containing blood or its components can be placed in the chamber, the at least one bag being permeable to gas, such as xenon gas. The chamber may be hermetically sealed. The chamber can be supplied with the gas, such as xenon, from the gas source such that the gas saturates the blood or its components.

The invention may also be embodied as a system for preserving blood and its components. The system can include a device having a body defining a chamber, the chamber being configured to receive at least one bag containing blood or its components, the at least one bag being permeable to gas, a cover hermetically sealable to the body, an inlet in fluid communication with the chamber, and a pressure indicator configured to indicate pressure in the chamber, the pressure indicator including a conduit containing a liquid. A portion of the conduit can be transparent such that the liquid is visible. A source of pressurized gas is in fluid communication with the inlet of the device, the source being configured to provide pressurized gas to the chamber.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

The present invention is generally embodied by a system, method, or device intended for preserving blood and/or its components (e.g. platelets) in a gaseous medium under pressure. In various embodiments, the blood and blood components, pressure, time and temperature are the same or similar to those described in U.S. Pat. Pub. No. 2010/0009334, now issued as U.S. Pat. No. 8,158,339, and U.S. Prov. No. 61/384,837, the disclosures of which are incorporated herein by reference. For ease of reading and comprehension, the term "bag of blood" should be generally understood to include a plurality of bags of blood or blood components (e.g. platelets).

Figure 1:
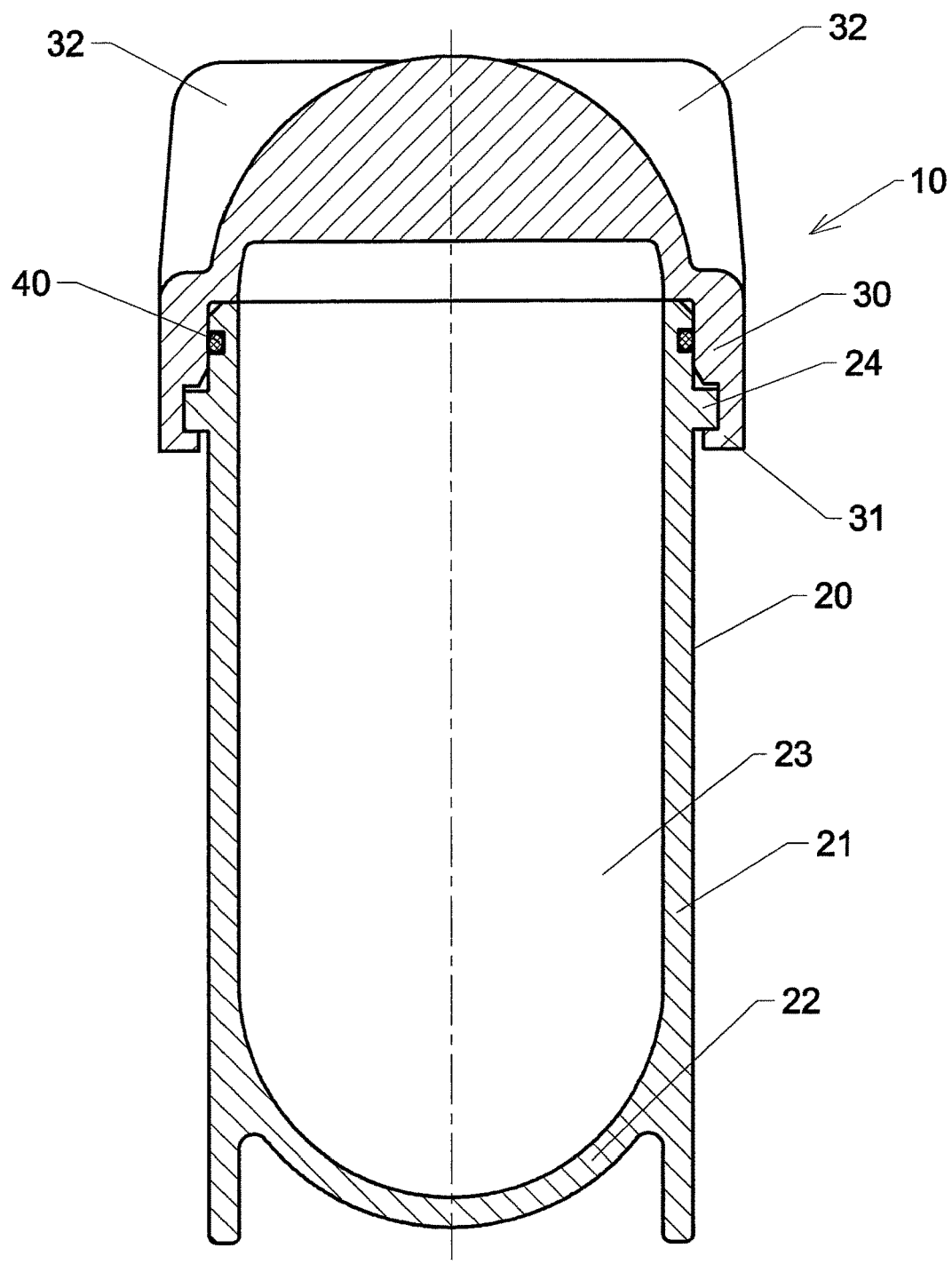
FIG. 1 is a cross-sectional view of a device in accordance with the present invention.

A first embodiment of the present invention is shown in FIG. 1. Device 10 is made as hermetically sealed chamber having body 20 and cover 30. Body 20 is made as a cylindrically shaped sleeve having side wall 21 and bottom 22, which form an internal space or chamber 23 intended for placing a bag (or several bags) of blood or its components (not shown).

Figure 2:
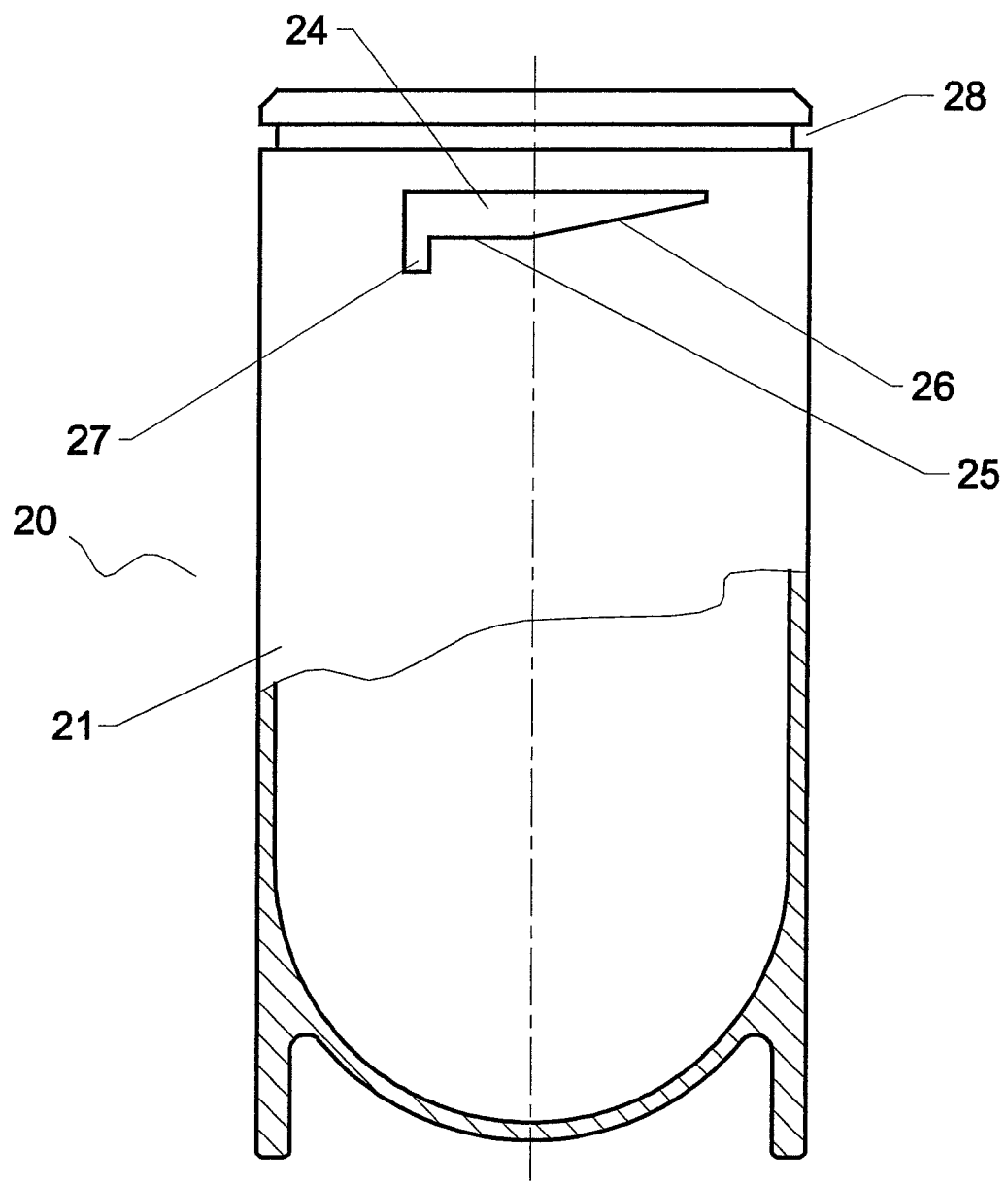
FIG. 2 is a partially cut away side view of the device according to FIG. 1.

In one embodiment, arc-shaped protrusions 24 (see FIG. 2) have mating surfaces, surface 25 which is parallel to cross-sectional plane of body 20, and surface 26, which is angled relative to the cross-sectional plane of body 20. Protrusions 24 have a stop plate 27 on the opposite side from surface 26. Protrusions 24 form a part of bayonet connection between cover 30 and body 20. Protrusions 31 on cover 30 mate by sliding over surfaces 26 and 25 when cover 30 is turned around to seal the device, which results in drawing cover 30 and body 20 together. Stop plates 27, into which protrusions 31 bear against when they reach end point, limit the angular turn when cover 30 is being closed. For convenience, the outside of the upper part of cover may have radial vanes 32 to facilitate turning (see FIG. 1). The cover 30 can alternatively be connected to the body 20 with other types of connectors, which hermetically seal the chamber 23. Hermetic sealing of the chamber 23 can be ensured by using appropriate seals between the body 20 and cover 30. For example, circular groove 28 may be provided on the outside of side wall 21 in the upper part of body 20 (above protrusions 24). Sealing ring 40, which provides hermetic sealing of cover 30 with body 20, may be placed into the circular groove (see FIG. 1). Body 20 and cover 30 can be made of rigid material (e.g. metal or plastic) and may be manufactured using known methods (e.g. pressure die casting). It is preferable that the bayonet connection is made as an integral unit with body 20 and cover 30.

Figure 3:
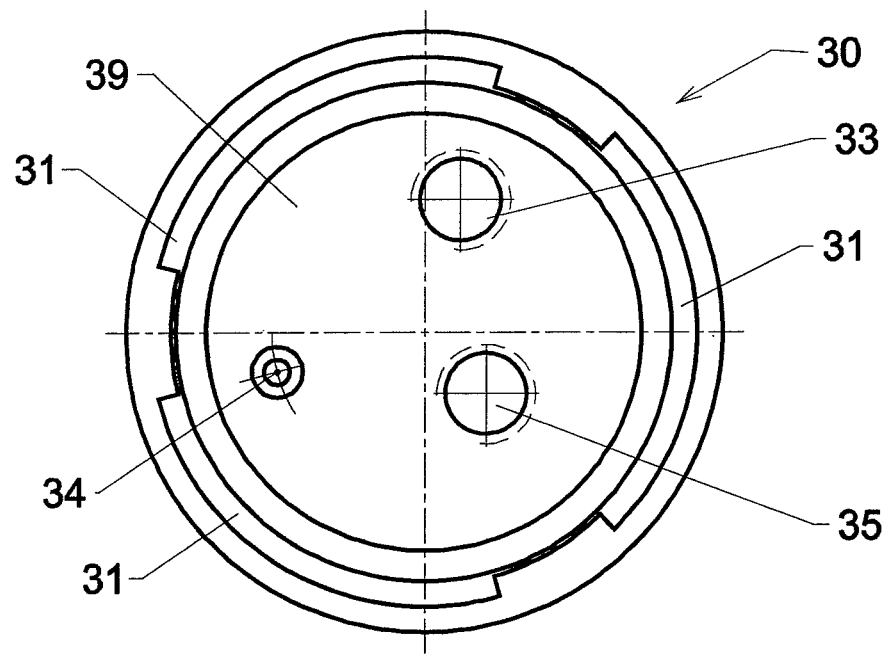
FIG. 3 is a top view of the device according to FIG. 1.
Figure 4:
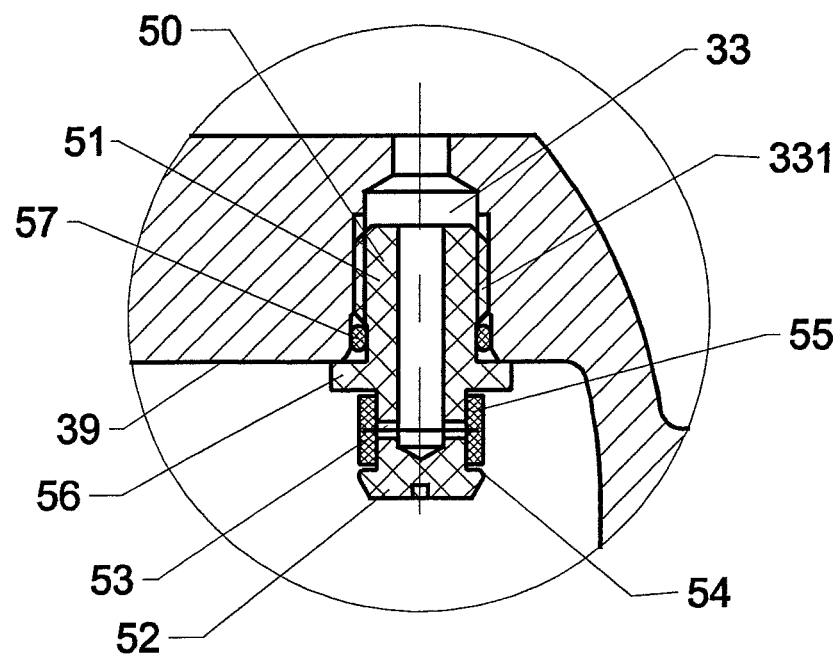
FIG. 4 is a cross-sectional detailed view of an inlet in accordance with the present invention.
Figure 5:
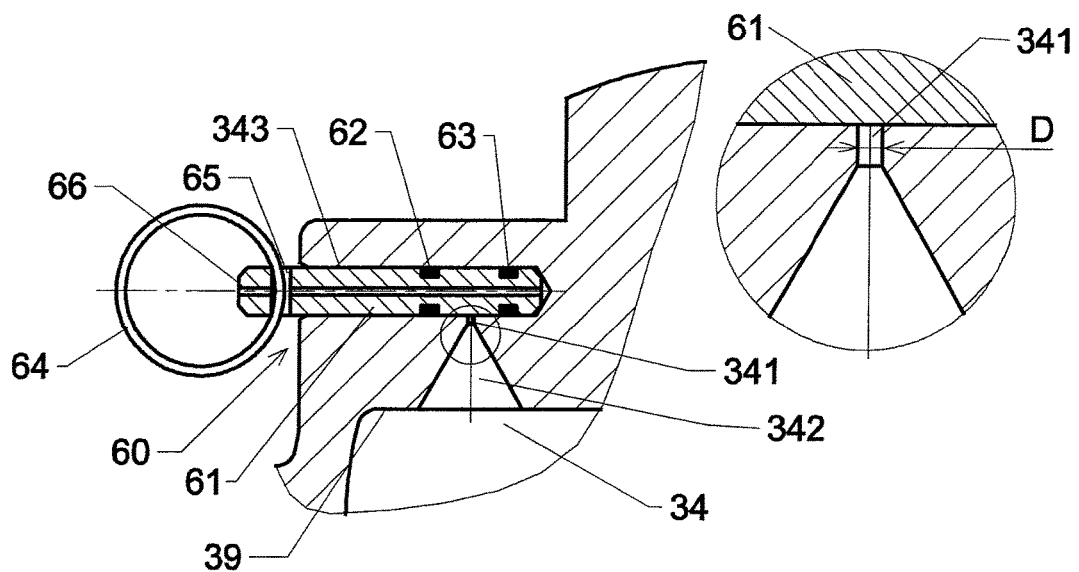
FIG. 5 is a cross-sectional detailed view of an outlet in accordance with the present invention and a detailed view of the outlet duct.

As shown in FIG. 3, cover 30 includes an inlet duct 33, and a non-return valve 50 (shown in detail in FIG. 4), which can be installed into the inlet duct. Non-return valve 50 is made as a sleeve with cylindrical side wall 51 and bottom 52. Several through holes 53 are made in side wall 51 near bottom 52. Circular groove 54 is made on the outside of side wall of the sleeve, and the through holes 53 are located in the area of circular groove 54. Ring 55, which may be made of an elastic material, has overlapping holes 53 in circular groove 54. Non-return valve 50 may have internal threads so that inlet duct 33 may be screwed into external thread 331 on side wall 51 of non-return valve 50 (on the side that is opposite to bottom 52). Non-return valve 50 may have stop member 56 made in the form of a collar on side wall 51, located between external thread 331 and circular groove 54. Stop member 56 can serve as a stopping element during installation of non-return valve 50 so that the stopping element 56 meets inner side 39 of cover 30.

Non-return valve 50 may operate in a conventional way. When gas is fed under pressure into chamber 23 through non-return valve 50, gas presses on ring 55 through holes 53. Due to the elastic material, segments of ring 55 bend off from holes 55, which allows the gas to pass into chamber 23. After the gas is turned off, ring 55 is pressed to holes 55, due to the increased pressure of gas in chamber 23 relative to atmospheric pressure, forming a hermetic seal, and thus preventing gas from flowing out of chamber 23.

Outlet duct 34 is made in cover 30, which connects the external side of cover 30 with its internal side. Lock valve 60 may be located in outlet duct 34. Outlet duct 34 has channel 341, connected with internal side 39 of cover 30 via frusto-conical part 342. Frusto-conical part 342 may help protect channel 341 against damage. In one embodiment, channel 341 has a section area no greater than 0.05 mm$^2$. Outer portion 343 may intersect channel 341 and be formed in the external side of cover 30. Lock valve 60 has stem 61, and is installed from the outside of cover 30 into outer portion 343 of outlet duct 34. Stem 61 may be installed in such a way that it overlaps channel 341 of outlet duct 34 at the point of its intersection with outer portion 343 of outlet duct 34. Stem 61 may include sealing rings 62 and 63 installed into circular grooves made on the outer surface of stem 61. Stem 61 may be installed in such a way that the point of intersection between channel 341 and outer portion 343 of outlet duct 34 is located between rings 62 and 63 so that a hermetic seal is formed.

Outlet duct 34 and lock valve 60 serve for unsealing chamber 23. Lock valve 60 may be placed to hermetically overlap outlet duct 34 to prevent gas from leaving chamber 23. Prior to removing cover 30 for the purpose of taking bags with preserved blood from chamber 23, lock valve 60 may be pulled out from outer portion 343 of outlet duct 34, to allow gas to leave chamber 23. Gas may slowly leave chamber 23, due to the small section area of channel 341 of outlet duct 34. Lock valve 60 may be equipped with ring 64 installed radially through hole 65 in stem 61 to make the removal of lock valve 60 more convenient for users. Stem 61 may be hollow and have axial channel 66 to allow air from outer portion 343 of outlet duct 34 to pass during the course of installation of lock valve 60 into the outer portion 343.

To lessen a possibility of abrupt pressure difference in chamber 23 in the course of unsealing, the section area of channel 341 of outlet duct 34 is preferably very small. However, it is not always feasible for outlet duct 34 to be small enough to protect against an abrupt loss of pressure in chamber 23, especially if cover 30 is made of plastic. Therefore, as an alternative to first portion 341 being small enough to control the rate of gas outflow, outlet duct 34 may have a relatively large section area and a gas-permeable membrane may be installed to regulate the rate of gas flow out of chamber 23.

Figure 6:
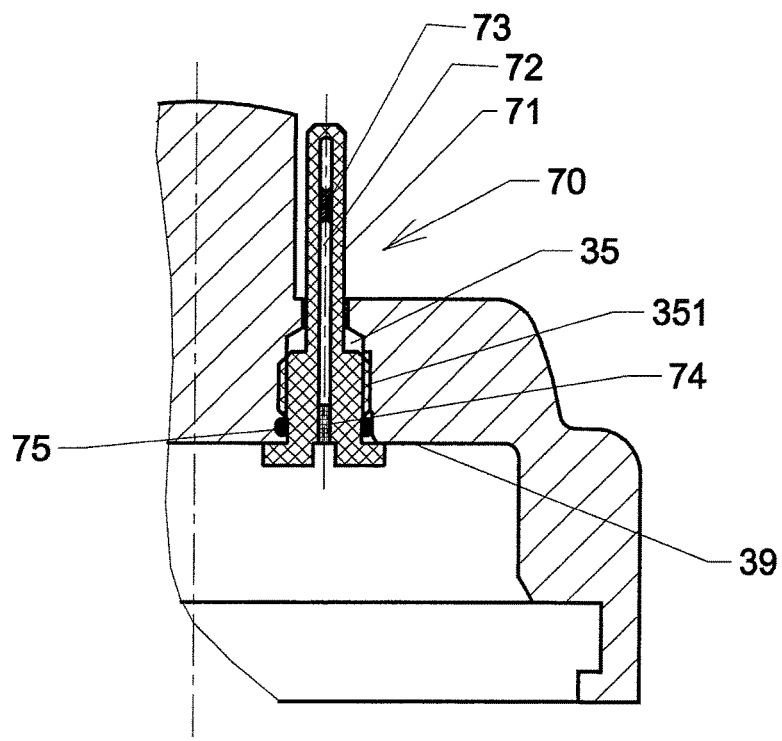
FIG. 6 is a cross-sectional detailed view of a pressure indicator on the cover of a device according to FIG. 1.

Cover 30 may also have control channel 35 extending from the external side of cover 30 to its internal side. Pressure indicator 70 (shown in FIG. 6) may be installed in control channel 35. Pressure indicator 70 may be made as a hollow rod 71 with an internal channel 72 of essentially cylindrical shape. In one embodiment, internal channel 72 may have a cross-sectional diameter of no greater than 1.5 mm, and be hermetically sealed on one end. On the other end, the pressure indicator 70 may have a thread for screwing it into control channel 35, corresponding to internal thread 351. Pressure indicator 70 may be installed so that open end of rod 71 faces internal surface 39 of cover 30, while its sealed end protrudes above the external surface of cover 30. Oil drop 73 is placed in the inner channel 72 of rod 71 (in the central portion of inner channel 72), and from the open end inner channel 72 is plugged by gas-permeable plug 74. Taking into account that position of oil drop 73 is directly related to the pressure of gas in chamber 23, the part of rod 71 protruding above the external surface of cover 30 is made of optically transparent material (e.g. polymethyl acrylate), which enables one to visually observe pressure. Hermetic sealing of installation of pressure indicator 70 is ensured by sealing ring 75.

When chamber 23 is in a closed, pressurized state, oil drop 73 is held in a top position (determined by pressure equilibrium on the both sides of oil drop 73) due to the pressure of gas passing through gas-permeable plug 74. When the pressure in chamber 23 decreases, gas oil drop 73 lowers from its top position. The oil drop 73 may stay in an area of rod 71 that is optically transparent, so that disruption to the pressure of chamber 23 can be visually determined based on the position of oil drop 73 in channel 72 of rod 71.

Device 10 may be used for preserving blood and its components according to the following method. Gas-permeable bags, capable of letting xenon to pass through, may be provided and filled with blood or its components. Polyolefin is one non-limiting example of a suitable material for which bags can be made. In particular, commercially available bags PL 2410 Storage Container 1000 produced by Fenwal Inc. (Drive Lake Zurich, Illinois) can be used for this purpose. After placing a bag (or several bags) containing blood or its components into body 20 (not shown), cover 30 may be mated with body 20, so that the bags are hermetically sealed in chamber 23. Chamber 23 may be filled with gas, in certain embodiments having a xenon content of no less than 65%, through inlet duct 33 and non-return valve 50 until the pressure in the chamber reaches the range of approximately 3.5 bars-5 bars, including all integers there and all numbers between consecutive integers to the tenth decimal point (i.e., 3.6, 3.7, 3.8 bars, etc.) The chamber may be filled with gas by a system (not shown), which may comprise a high-pressure vessel with a gas and pipework with manometer and control valve hermetically connected to inlet duct 33 located on the external surface of cover 30. Device 10 may be placed into a refrigerator for storage at a temperature within 3° C.-6° C. Due to the fact that bags are made of gas-permeable material, the blood contained in them may be saturated with xenon to produce conditions (i.e., namely, gas pressure and temperature) for the preservation of blood and blood components as described in U.S. Pat. No. 8,158,339. Device 10 may be stored in a refrigerator a temperature within 3° C.-6° C. for a period of time from several hours to fourteen days, or longer.

Prior to using the preserved blood or its components, device 10 can be removed from a refrigerator, and the lock valve 60 can be removed. After pressure is lowered in chamber 23, cover 30 may be opened and bags with blood or blood components are taken out. Before using the bag or bags with blood or its components, it may be desirable to allow the bag or bags to sit until they naturally return to room temperature, as well as allow the gas pressure inside the bags to return to atmospheric pressure.

Because blood or its components can be stored in a refrigerator for a period of up to 14 days, it may be important to check whether the chamber has substantially maintained its pressure during storage. It may also be important to check whether the temperature of device 10 has increased above a specified storage temperature period during storage. Gas pressure in chamber 23 may be visually checked by means of pressure indicator 70 (as described above). Temperature sensors can be used for temperature control. For example a temperature sensor may be capable of fixing a maximum temperature during storage period. An example of suitable sensors are liquid-crystal temperature indicators produced under the trademark HemoTemp® by Biosynergy, Elk (Grove Village, Ill.). Other suitable sensors may be temperature indicators that are based on paraffin compounds having phase transition in the area of controlled values of temperature. One such temperature indicator is sold under trade name Check-Spot (produced by Harald H. Temmel KEG, Gleisdorf, Austria). These indicators are particularly well-suited for use with the present invention as they are made as tags with a self-adhesive surface, which may be attached to bags with blood as the bags are put into a refrigerator for storage. The temperature-sensitive agent on these indicators will change color according to the temperature. Indicators may be applied to bags with blood or its components so that the temperature indicator can indicate (for example, based on color) whether the temperature has increased during the storage of the bags, thereby alerting a user as to whether the blood or its components are suitable for use.

Thus, the present invention allows the use of simple and inexpensive bags made of gas-permeable material for the purpose of preserving blood and its components in a gas medium under pressure and storing them. The present invention also provides for the control of gas pressure, under which blood is being stored.

The invention may also be embodied as a method of preserving blood or it components. Bags of blood or its components may be provided. The bags may be made of gas-permeable material capable of letting xenon to pass through. The gas-permeable bags allow xenon-containing gas, which is fed into the chamber under pressure, to pass through the bag walls so that blood or its components contained in the bag may be saturated with xenon. The chamber may be cooled to a temperature of approximately 3-6° C. to provide preservation of blood or its components contained in the bag. The chamber may be stored in a refrigerator.

In one embodiment of the present invention, a bag of blood or its components or blood components separate from whole blood components, made of material gas-permeable for xenon, is placed into a hermetically sealed chamber. Xenon-containing gas or pure Xenon is fed under pressure through a non-return valve from a gas source (e.g., pressure vessel). After a pre-specified value of gas pressure inside the chamber is attained, gas is no longer fed into the chamber, and the gas source may be disconnected from the chamber. A non-return valve may prevent xenon gas from escaping the chamber. It is considered that this process in various embodiments results in saturation of the blood or components with xenon. Filling the chamber with gas may saturate blood or its components in the bag. After the chamber is filled, the blood or its components may be cooled and stored. The blood or its components may be cooled and stored in a refrigerator. Prior to the use of the blood or its components, the chamber may be taken out from the refrigerator and then depressurized (e.g., the chamber is opened and gets heated in a natural manner to approximately room temperature). Because xenon-containing gas may remain in the bag with preserved blood, it may be necessary to wait for 1-3 hours to allow this gas to pass through the walls of the bag. After preservation, the blood or its components may be used in a conventional manner.

Because pressurized gas can be fed into a chamber surrounding a bag containing blood or its components, and not directly fed into such a bag, the likelihood of bag tearing, due to excessive pressure of gas inside the bag, is lessened or eliminated. The method claimed herein allows the use of simple and inexpensive bags in the preservation of blood or its components at low temperatures based on saturation with xenon under pressure per U.S. Pat. No. 8,158,339. This results in significantly reduced expenses for preservation of blood or its components and upgrades the reliability of preservation due to the decreased likelihood of bag tearing due to pressure change.

What is claimed is:

1. A method for preserving blood and its components for later use, comprising:
   providing at least one bag containing blood or its components, said bag at least partially permeable to xenon gas;
   providing a device, said device including:
      a body defining a chamber, said chamber being configured to receive fully said at least one bag;
      a removable cover that is removably hermetically sealable to said body to seal all of said bag in said chamber;
      a fluid inlet in fluid communication with said chamber when the cover is removably connected to said body;
      a pressure indicator configured to indicate pressure in said chamber when the cover is removably connected to said body, at least a portion of said pressure indicator located external of an outer surface of said body, said pressure indicator in fluid communication with said chamber when the cover is removably connected to said body; and a pressure inlet and an outlet duct, said pressure inlet and said outlet duct in fluid communication with said chamber when said cover is connected to said body, said fluid inlet having a non-return valve positioned in said fluid inlet, said non-return valve including a sleeve and a ring, said sleeve having a plurality of openings in a bottom portion of said sleeve, said ring formed of an elastic material and positioned about an outer surface of said sleeve to overlie all of said plurality of openings, said sleeve including a radial projection to maintain a position of said ring relative to said sleeve, said non-return valve configured to control a flow of fluid through said fluid inlet, said pressure inlet having said pressure indicator at least partially positioned in said pressure inlet, said outlet duct including a movable plug that is configured to allow fluid in said chamber to escape said chamber when said plug is moved to a non-closed position;

placing said at least one bag in said chamber of said device;

placing said cover on said body of said device to hermetically seal said at least one bag in said chamber;

providing a source of xenon gas; and supplying said chamber with xenon gas from said source of xenon gas via said fluid inlet in said cover while said at least one bag is hermetically sealed in said chamber such that said xenon gas at least partially saturates said blood or its components in said at least one bag, said source of xenon gas supplied to said chamber of said device at pressure exceeding 1 atm.

2. A method for preserving blood and its components for later use, comprising:

providing at least one bag containing blood or its components, said bag at least partially permeable to xenon gas;

providing a device, said device including:
  a body defining a chamber, said chamber being configured to receive fully said at least one bag;
  a removable cover that is removably hermetically sealable to said body to seal all of said bag in said chamber;
  a fluid inlet in fluid communication with said chamber when the cover is removably connected to said body, a valve in said fluid inlet is a non-return valve, said valve including a sleeve and a ring, said sleeve having a plurality of openings in a bottom portion of said sleeve, said ring formed of an elastic material and positioned about an outer surface of said sleeve to overlie all of said plurality of openings, said sleeve including a radial projection to maintain a position of said ring relative to said sleeve;
  a pressure indicator configured to indicate pressure in said chamber when the cover is removably connected to said body, at least a portion of said pressure indicator located external of an outer surface of said body, said pressure indicator in fluid communication with said chamber when the cover is removably connected to said body;

placing said at least one bag in said chamber of said device;

placing said cover on said body of said device to hermetically seal said at least one bag in said chamber;

providing a source of xenon gas; and supplying said chamber with xenon gas from said source of xenon gas via said fluid inlet in said cover while said at least one bag is hermetically sealed in said chamber such that said xenon gas at least partially saturates said blood or its components in said at least one bag, said source of xenon gas supplied to said chamber of said device at pressure exceeding 1 atm.

3. The method as defined in claim 2, wherein said pressure indicator includes a conduit containing a liquid that is movable based on a pressure in said chamber, a portion of said conduit is transparent such that movement of the liquid in the conduit is visible outside said chamber while said cover is hermetically sealed to said body.

4. The method as defined in claim 1, wherein said pressure indicator includes a conduit containing a liquid that is movable based on a pressure in said chamber, a portion of said conduit is transparent such that movement of the liquid in the conduit is visible outside said chamber while said cover is hermetically sealed to said body.

5. The method as defined in claim 1, wherein said pressure indicator includes a hollow rod having an internal channel that is at least partially filled with a liquid, a cross-diameter of said hollow rod is up to 1.5 mm, a first end of said hollow rod is hermetically sealed and a second end of said hollow rod is in fluid communication with said chamber when said cover is hermetically sealed to said body, said second end including a gas-permeable plug to enable gas to flow through said plug while preventing said liquid from flowing through said plug, at least a portion of said hollow rod visible outside said chamber when said cover is hermetically sealed to said body and formed of an optically transparent material.

6. The method as defined in claim 2, wherein said pressure indicator includes a hollow rod having an internal channel that is at least partially filled with a liquid, a cross-diameter of said hollow rod is up to 1.5 mm, a first end of said hollow rod is hermetically sealed and a second end of said hollow rod is in fluid communication with said chamber when said cover is hermetically sealed to said body, said second end including a gas-permeable plug to enable gas to flow through said plug while preventing said liquid from flowing through said plug, at least a portion of said hollow rod visible outside said chamber when said cover is hermetically sealed to said body and formed of an optically transparent material.

7. The method as defined in claim 4, wherein said pressure indicator includes a hollow rod having an internal channel that is at least partially filled with a liquid, a cross-diameter of said hollow rod is up to 1.5 mm, a first end of said hollow rod is hermetically sealed and a second end of said hollow rod is in fluid communication with said chamber when said cover is hermetically sealed to said body, said second end including a gas-permeable plug to enable gas to flow through said plug while preventing said liquid from flowing through said plug, at least a portion of said hollow rod visible outside said chamber when said cover is hermetically sealed to said body and formed of an optically transparent material.

8. The method as defined in claim 1, wherein said outlet duct includes an inner portion and an outer portion, said inner portion meeting said outer portion at a channel having a cross-sectional area of no greater than 0.05 mm$^2$, said outer portion being configured to slidably receive said lock valve, at least a portion of said lock valve overlying said channel and hermetically sealing said channel when said lock valve is in a lock position, said lock valve allowing fluid flow through said channel when said lock valve is in an unlocked position, said lock valve including a sealing arrangement to facilitate in said hermetic sealing of said channel when said lock valve is in a lock position, said lock valve including a handle to facilitate movement of said lock valve between said lock position and unlock position, said inner portion having a frusto-conical shape having an apex and a base, said channel being located at said apex of said inner portion, said base opening toward said chamber when said cover is connected to said body.

9. The method as defined in claim 7, wherein said outlet duct includes an inner portion and an outer portion, said inner portion meeting said outer portion at a channel having a cross-sectional area of no greater than 0.05 mm$^2$, said outer portion being configured to slidably receive said lock valve, at least a portion of said lock valve overlying said channel and hermetically sealing said channel when said lock valve is in a lock position, said lock valve allowing fluid flow through said channel when said lock valve is in an unlocked position, said lock valve including a sealing arrangement to facilitate in said hermetic sealing of said channel when said lock valve is in a lock position, said lock valve including a handle to facilitate movement of said lock valve between said lock position and unlock position, said inner portion having a frusto-conical shape having an apex and a base, said channel being located at said apex of said inner portion, said base opening toward said chamber when said cover is connected to said body.

10. The method as defined in claim 1, wherein said fluid inlet, said pressure inlet, and said outlet duct are located on said cover.

11. The method as defined in claim 9, wherein said fluid inlet, said pressure inlet, and said outlet duct are located on said cover.

12. The method as defined in claim 1, said cover includes a receiving slot and an outer surface of said body includes a bayonet, said receiving slot being configured to mate with said bayonet to secure said cover to said body when said cover is rotated relative to said body, said bayonet including a first mating surface that is parallel to a cross-sectional plane of said body and a second mating surface that is angled relative to said cross-sectional plane of said body, a front end of said first mating surface is connected to a back end of said second mating surface, a back end of said first mating surface including a stop to prevent further rotation of said cover on said body while said cover is removably connected to said body, at least a portion of said bayonet that includes said second mating surface is narrower than said portion of said bayonet that includes said first mating surface.

13. The method as defined in claim 2, said cover includes a receiving slot and an outer surface of said body includes a bayonet, said receiving slot being configured to mate with said bayonet to secure said cover to said body when said cover is rotated relative to said body, said bayonet including a first mating surface that is parallel to a cross-sectional plane of said body and a second mating surface that is angled relative to said cross-sectional plane of said body, a front end of said first mating surface is connected to a back end of said second mating surface, a back end of said first mating surface including a stop to prevent further rotation of said cover on said body while said cover is removably connected to said body, at least a portion of said bayonet that includes said second mating surface is narrower than said portion of said bayonet that includes said first mating surface.

14. The method as defined in claim 11, said cover includes a receiving slot and an outer surface of said body includes a bayonet, said receiving slot being configured to mate with said bayonet to secure said cover to said body when said cover is rotated relative to said body, said bayonet including a first mating surface that is parallel to a cross-sectional plane of said body and a second mating surface that is angled relative to said cross-sectional plane of said body, a front end of said first mating surface is connected to a back end of said second mating surface, a back end of said first mating surface including a stop to prevent further rotation of said cover on said body while said cover is removably connected to said body, at least a portion of said bayonet that includes said second mating surface is narrower than said portion of said bayonet that includes said first mating surface.

15. The method as defined in claim 1, wherein said body includes a body groove positioned below a top surface of said body and a sealing ring at least partially positioned in said body groove, said sealing ring configured to facilitate in forming a hermetic seal between said cover and said body when said cover is removably connected to said body.

16. The method as defined in claim 14, wherein said body includes a body groove positioned below a top surface of said body and a sealing ring at least partially positioned in said body groove, said sealing ring configured to facilitate in forming a hermetic seal between said cover and said body when said cover is removably connected to said body.

17. The method as defined in claim 1, further including the steps of cooling said blood or its components to a temperature from 3° C. to 6° C. while said bag is hermetically sealed in said chamber and exposed to said source of xenon gas.

18. The method as defined in claim 2, further including the steps of cooling said blood or its components to a temperature from 3° C. to 6° C. while said bag is hermetically sealed in said chamber and exposed to said source of xenon gas.

19. The method as defined in claim 16, further including the steps of cooling said blood or its components to a temperature from 3° C. to 6° C. while said bag is hermetically sealed in said chamber and exposed to said source of xenon gas.

20. The method as defined in claim 1, wherein said pressure of said xenon gas in said chamber while said bag is hermetically sealed in said chamber is 3.5 bars-5 bars, said source of xenon gas including at least 65 vol. % xenon gas.

21. The method as defined in claim 2, wherein said pressure of said xenon gas in said chamber while said bag is hermetically sealed in said chamber is 3.5 bars-5 bars, said source of xenon gas including at least 65 vol. % xenon gas.

22. The method as defined in claim 19, wherein said pressure of said xenon gas in said chamber while said bag is hermetically sealed in said chamber is 3.5 bars-5 bars, said source of xenon gas including at least 65 vol. % xenon gas.

23. The method as defined in claim 1, further including the steps of maintaining said bag in said chamber for up to 14 days, at least partially removing said source of xenon gas from said chamber prior to removing said cover from said base, removing said cover from said base after a pressure in said chamber has been reduced, allowing xenon gas to diffuse out of said bag for at least one hour.

24. The method as defined in claim 2, further including the steps of maintaining said bag in said chamber for up to 14 days, at least partially removing said source of xenon gas from said chamber prior to removing said cover from said base, removing said cover from said base after a pressure in said chamber has been reduced, allowing xenon gas to diffuse out of said bag for at least one hour.

25. The method as defined in claim 22, further including the steps of maintaining said bag in said chamber for up to 14 days, at least partially removing said source of xenon gas from said chamber prior to removing said cover from said base, removing said cover from said base after a pressure in said chamber has been reduced, allowing xenon gas to diffuse out of said bag for at least one hour.

26. The method as defined in claim 8, wherein said radial projection includes an external thread and said handle includes a ring.

\* \* \* \* \*